(12) United States Patent
Walter

(10) Patent No.: US 6,247,927 B1
(45) Date of Patent: Jun. 19, 2001

(54) DISPOSABLE ARTICULATOR HAVING TRAY SUPPORT WITH OPENING WHICH ACCEPTS A PROJECTION FROM A TRAY

(75) Inventor: Jose Walter, Herndon, VA (US)

(73) Assignee: Cbite, Inc., Clifton, VA (US)

( * ) Notice: Subject to any disclaimer, the term of this patent is extended or adjusted under 35 U.S.C. 154(b) by 0 days.

(21) Appl. No.: 09/424,369
(22) PCT Filed: Jul. 22, 1999
(86) PCT No.: PCT/US99/16508
§ 371 Date: Nov. 23, 1999
§ 102(e) Date: Nov. 23, 1999

Related U.S. Application Data
(60) Provisional application No. 60/093,868, filed on Jul. 23, 1998, and provisional application No. 60/096,532, filed on Aug. 13, 1998.

(51) Int. Cl.[7] .................................................. A61C 11/00
(52) U.S. Cl. ............................................. 433/60; 433/54
(58) Field of Search .................................. 433/34, 54, 57, 433/60, 64, 74

(56) References Cited

U.S. PATENT DOCUMENTS

| 3,581,398 | * | 6/1971 | Thomas . | |
|---|---|---|---|---|
| 3,702,027 | * | 11/1972 | Marshall et al. . | |
| 4,439,151 | * | 3/1984 | Whelan | 433/60 |
| 4,508,506 | * | 4/1985 | Jackson | 433/74 |
| 4,608,016 | * | 8/1986 | Zeiser | 433/74 |
| 4,767,330 | * | 8/1988 | Burger | 433/213 |
| 5,129,822 | * | 7/1992 | Dobbs | 433/34 |
| 5,393,227 | * | 2/1995 | Nooning | 433/74 |
| 5,957,688 | * | 9/1999 | Van Valey | 433/60 |
| 6,099,305 | * | 8/2000 | Browne | 433/34 |

* cited by examiner

Primary Examiner—Ralph A. Lewis
(74) Attorney, Agent, or Firm—Glenna Hendricks

(57) ABSTRACT

This invention provides a device for use in making dental models comprising a tray support a having an opening and a tray having an inferior surface with a projection from said inferior surface of said tray, wherein said projection of said tray fits into said opening in said tray support, said tray support having attached thereto hinge portions which are capable of interaction with hinge portions from a second tray support to form a completed hinge means.

12 Claims, 4 Drawing Sheets

DISPOSABLE ARTICULATOR HAVING TRAY SUPPORT WITH OPENING WHICH ACCEPTS A PROJECTION FROM A TRAY

This application takes priority from PCT application US99/16508, which claims priority from U.S. Provisional Patent Application No. 60/096,868 filed on Jul. 23, 1998 and No. 60/096,532 filed on Aug. 13, 1998.

FIELD OF THE INVENTION

This invention relates to an apparatus for making dental models for use in production of bridges, crowns, and other restorative articles.

BACKGROUND OF THE INVENTION

The production of restorative objects such as crowns, bridges and tooth prostheses requires use of dental models from which to work. The production of such models are first created using a negative impression of the teeth. The negative impression is then filled with casting materials which harden, thus creating models of the patient's teeth. In order to work with these models, the casting material must be sawed into smaller pieces. It is essential to be able to realign the pieces in the appropriate manner.

In making of models, the technician uses a device known as an articulator, which is an instrument which simulates the movements of the mandible and aids in the construction of dental restorations.

The prior art includes several devices for use in making the models. U.S. Pat. No. 4,398,884 to Huffman, which describes an insert which locks onto the casting material to guide removal of model teeth during insertion into and withdrawal from the dental model presents on approach to the need to divide, then reassemble the models. However, the devices disclosed therein do not provide means for relating the maxillary and mandibular dental arches with one another in such a way as to create an accurate three-dimensional model showing the arches as they were at the time the mold was made.

U.S. Pat. No. 5,466,152 to Walter discloses and claims a dental articulator system containing a plurality of holes in the tray support into which pins are inserted before the casting material is placed into the tray. The pins provide indexing means for reassembly of the model after it has been divided into smaller pieces. The need for pins has been eliminated with the instant invention.

Other articulators on the market include some which require a separable joint which must be glued in place or very expensive metal devices which require considerable time and expense to use.

SUMMARY OF THE INVENTION

The instant invention provides an articulator having trays with a projection on the inferior surface which fits into a corresponding opening in a tray support. The two trays in the tray supports are assembled as mirrored parts connected with a hinge means. When two parts are interlocked with a hinge means the hinges allow movement both laterally and horizontally during interaction with the impression. The tray support opening has one or more indexing means provided by a shape which allows the projection from the inferior aspect of the tray having corresponding indexing means to fit in only one orientation into the opening. As an example, for purposes of indexing, the projection from the tray and the tray support opening may be wider at the end closest to the hinge means, with the corresponding opening of the tray support gradually narrowing as it proceeds toward the free end of the tray support. Similarly, the projection on the inferior surface side of the tray may have indexing means such as ribs (ridges), waves or other irregularities which fit snugly into complementary openings of the tray support so that said projection fits in only one orientation in the corresponding opening of the tray support. The particular variations in shape are irrelevant, so long as they allow the projection from the inferior aspect of the tray to fit in the opening of the tray support in only one orientation so that when the trays with the casting material area removed and segmented they can be reassembled in the tray supports with accuracy.

DETAILED DESCRIPTION OF THE INVENTION

Figure 1:
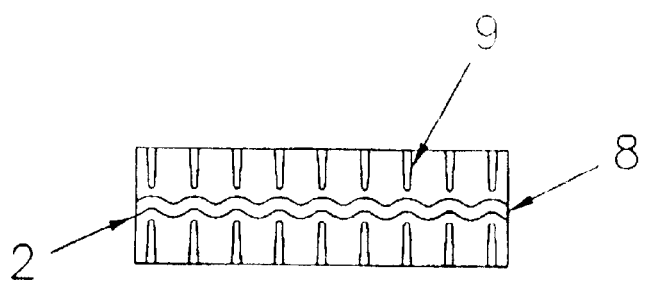
FIG. 1 is a top planar view of a tray for holding casting material such as plaster or stone.

It is the purpose of this invention to provide a dental articulation apparatus which will eliminate work and costs associated with use of the presently known articulators. The apparatus permits the user to make accurate models from impressions obtained by dentists doing restorative work. When fully assembled, the apparatus provides maxillary and mandibular tray support members with trays which have on one surface (herein designated the inferior surface) at least one projection that fits into an opening in the tray support. In use, a negative dental impression may be filled with a casting material. The two halves of the articulator (the trays on the supports, wherein the two halves are made to interact by hinge means) are manipulated on said hinge means so that the tray on one half is pressed into the casting material in the mold formed by the negative dental impression. After the casting material has hardened, the opposing side of the negative impression is filled with casting material and the empty tray on the support of the second half of the articulator (tray on support) is manipulated on the hinge means so that it presses into the casting material of the negative impression. After the casting material has hardened, the negative impression is removed. The entire articulator then has models of the maxillary and mandibular teeth on the trays. Alternatively, each tray may be loaded with casting material which is allowed to harden slightly. The casting material is formed into models by pressing said casting material into the appropriate impressions. Once the casting material has hardened sufficiently, the trays and supports with the casting material are removed from the impression. When the casting material has fully hardened, the tray with the models can be removed from the tray support. The tray with the models of the teeth may then be worked on as a unit or, as is more often the case, may be segmented. If the support has an opening which will accept the projection from the tray in only one orientation such as having varying width and/or other irregularities such as waves or ribs in the sides complementary to irregularities in the sides on the projection on the inferior surface of the tray, the models are easily re-assembled in the appropriate tray support in the correct order. The support means has an extension which is attached to a hinge means.

In this disclosure, the surface of the tray support which interfaces with the tray when the device is assembled has been designated the superior surface of the support, while the side opposite the surface upon which the tray sits is designated the inferior surface of the tray support. The surface of the tray which interfaces with the support when the device is fully assembled has been, herein, designated the inferior surface of the tray, and the surface of the tray which interfaces with the casting material is designated herein as the superior surface. In the drawings, when any number appears on more than one figure, the number always represents the same structure.

The articulator of the invention presents several advantages over prior art articulators. Because the entire apparatus is made from plastic, the apparatus is easy to work with. A strong plastic with a small amount of flexibility is most appropriate for use in making the device. The device of this invention does not require pegs or pins for use in indexing the models.

Referring to the drawings,, FIG. 1 is a top plane view of the superior surface of the tray (2) which holds the model, said tray having a projection (8) in the center and smaller anti-rotation guide means (9). Anti-rotational means may be convex (protruding above the tray surface) or concave (indentations in the tray surface).

Figure 2:
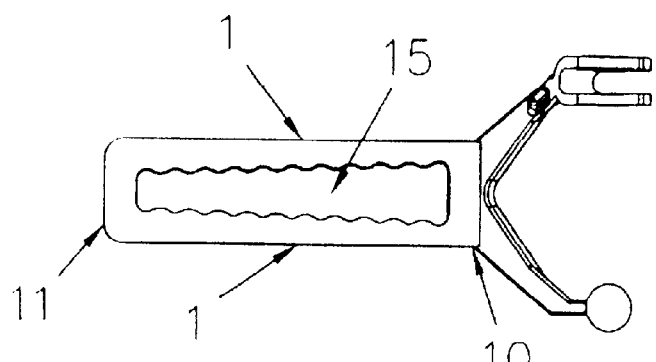
FIG. 2 is a view from above of the tray support.
Figure 3:
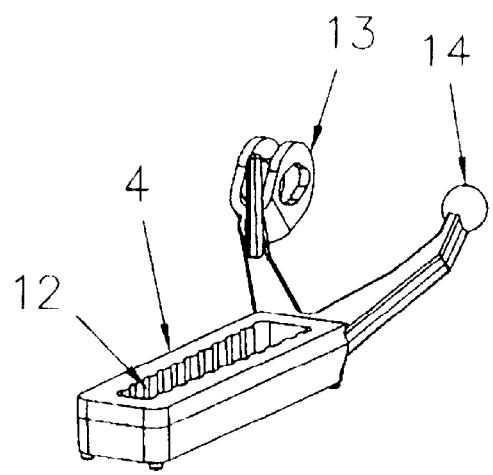
FIG. 3 is a perspective view of the tray support.
Figure 4:
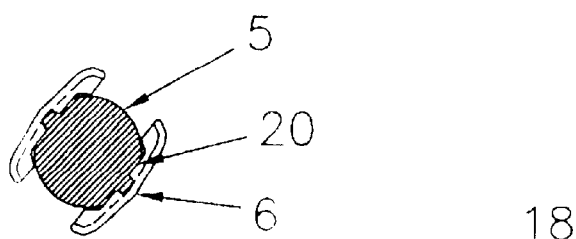
FIG. 4 shows detail of a ball and socket type hinge.

FIG. 2 shows the support tray with sides (1) from above (viewing the superior surface) with the opening (15) which accepts the projection(s) from the inferior surface of the tray. The support tray has a hinge end (10) and a free end (11). The tray support is shown in FIG. 3 in perspective of the support tray showing the superior surface (4) of the support tray and the sides of the corresponding opening (12) (which, in this case, is scored to accept a ribbed projection) into which the projection from the inferior surface of the tray will fit. The hinge means has a ball (14) and ball acceptor portion (13). An identical support may be interlocked via a ball and acceptor on an identical tray support when assembling the device. FIG. 4 shows an enlargement of the ball and acceptor when interlocked. The ball (5) has notches (20) which fit into recesses (6) in the acceptor portion of the support tray.

Figure 5:
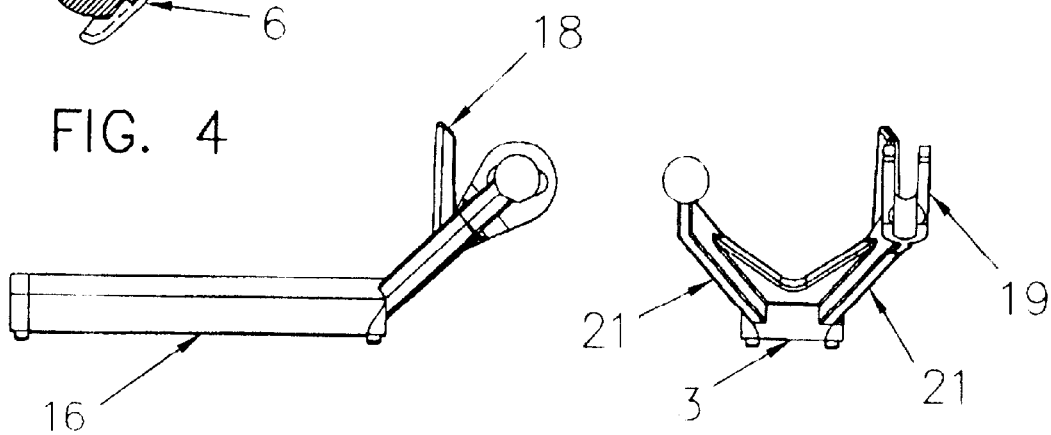
FIG. 5 is a lateral view of the tray support.
Figure 6:
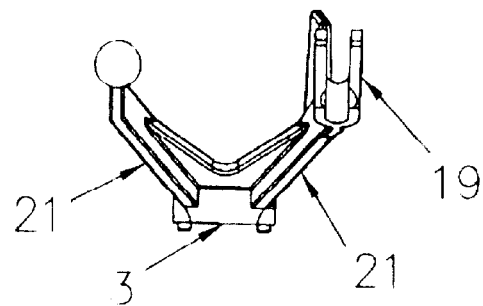
FIG. 6 shows a posterior view of a ball and socket hinge means.

FIG. 5 shows a lateral view of the tray support having a free end stop (18) which causes the tray supports with the trays to stop once the approaching parts have reached a position which is parallel with each other. FIG. 6 shows a posterior view of the ball and socket hinge means showing notches (19) in the acceptor means which guide the ball portion into the proper location within the acceptor. A bridge (3), which may be a part of the wall of the support tray wall, holds each arm (21) of the hinge means in proper alignment.

While the wavy configuration is useful to enhance correct orientation of the model in the tray holder, other configurations such as saw tooth-shaped variation in the sides could be used.

Figure 7:
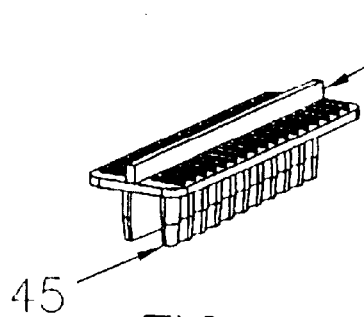
FIG. 7 shows a perspective view of a tray.
Figure 8:
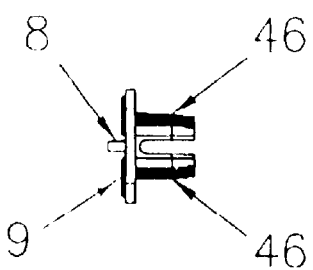
FIG. 8 shows an end-on view of a tray.

FIG. 7 is provided as a perspective view of the tray from above showing the superior surface of the tray with view of the medial projection (8). FIG. 8 provides an end-on view of the tray with projection (46) (in this case, divided by a channel) with view of the anti-rotational means (9) and medial projection (8) on the superior surface of the tray.

Figure 9:
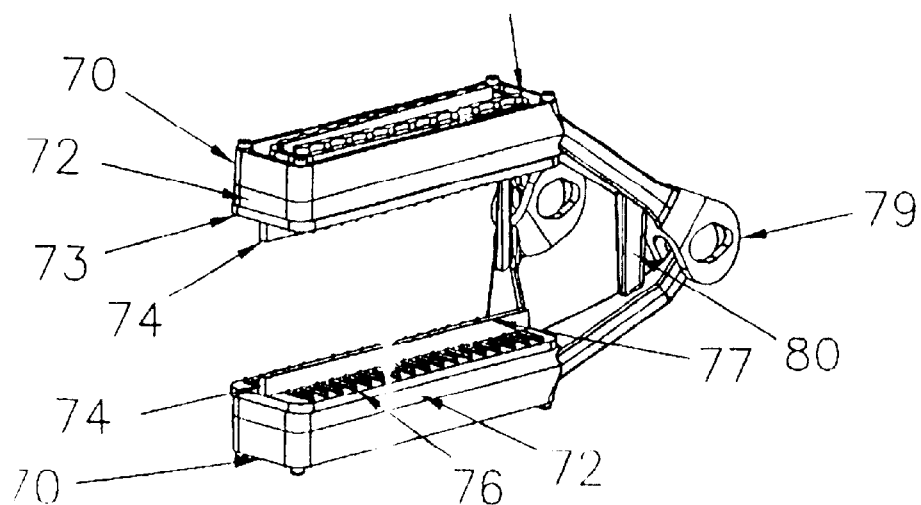
FIG. 9 shows the trays with tray supports fully assembled.

FIG. 9 shows the trays on supports fully assembled for use with a dental impression. The parts are, particularly, the tray support (70), with the tray (72) placed thereon. The protrusion (71) from the inferior surface of the tray can be seen projecting through the opening in the tray support. In this particular embodiment, the tray has a lip (73) which overhangs the side of the tray support for easy removal of the tray from the tray support. The end stop (80) is in place to prevent over closure at the hinge. The joint (79) is a ball and acceptor joint. The projections on the superior surfaces of the trays to which casting material is applied are designated (74) and the anti-rotational means as (76) in this drawing.

Figure 10:
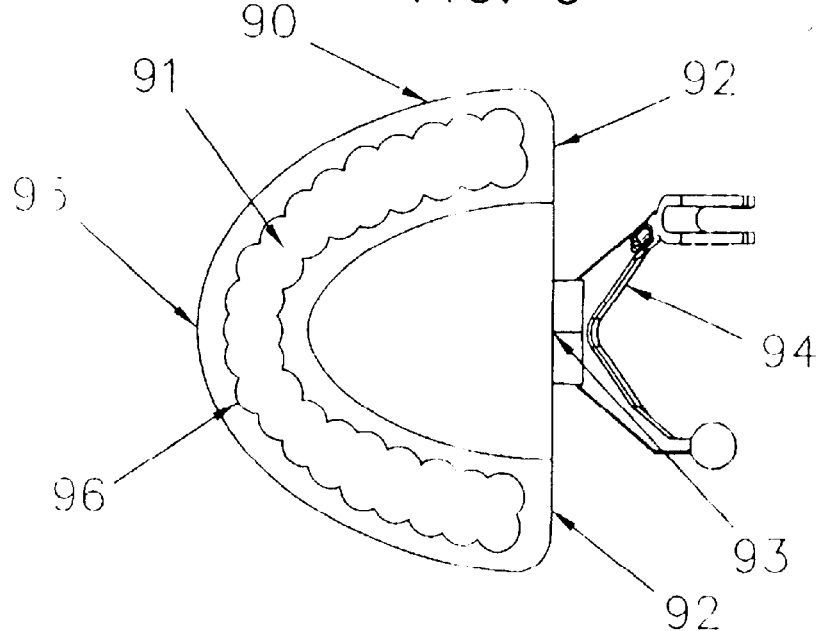
FIG. 10 shows a tray support in a horse shoe shape for purposes of making a dental model of both sides of an entire jaw at one time.

The articulator may be made in a horse shoe shape for purposes of making a dental model of both sides of an entire jaw at one time. Referring to the figures, FIG. 10 shows a support tray (90) with an curved section (95) and two lateral ends (96) which correspond to the location of the molars. Viewing toward the superior surface, there is an opening (91) with sides (92) having irregular surface (in this instance, wave-like configuration) and having a bridge (93) which is an attachment means for the hinge means (94). The bridge attaches in such a manner that it holds the support tray in alignment, but allows sufficient movement to provide optimum articulation with the impression.

Figure 11:
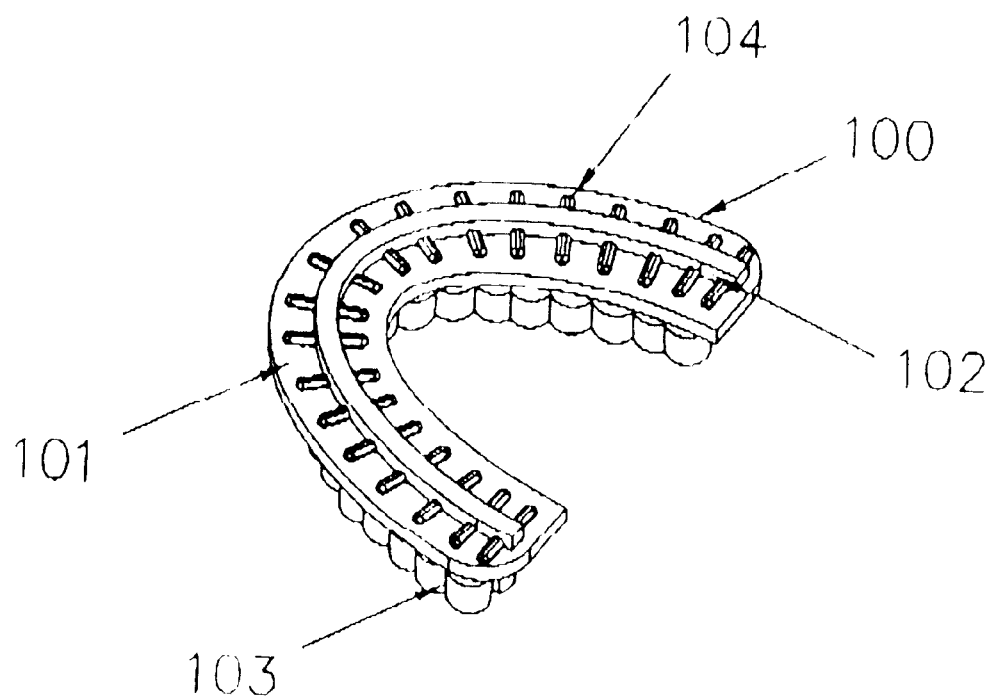
FIG. 11 shows the tray which fits into the tray support of FIG. 10.

FIG. 11 shows the horse shoe shaped tray (100) with a superior surface (101) which holds the casting material. Emerging from the superior surface there is a projection (102) which is equivalent to the projection (8) in FIG. 8. The tray also has a projection (103) from the inferior surface of the tray which is sculpted to fit snugly into the opening (96) of the tray of FIG. 10. The tray also has smaller irregularities which serve as anti-rotational means (104).

Figure 12:
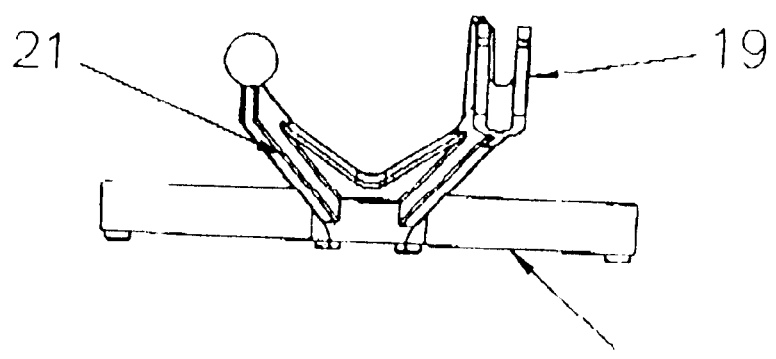
FIG. 12 shows a ball and socket hinge means for use with a horse shoe shaped support tray.

FIG. 12 is roughly the equivalent of FIG. 6, but has a broader bridge (106) to bridge the expanse across the portion of the tray at the ends of the horse shoe ((92) of FIG. 10). In this figure, (20) and (19) have the same designation as in FIG. 6.)

Figure 13:
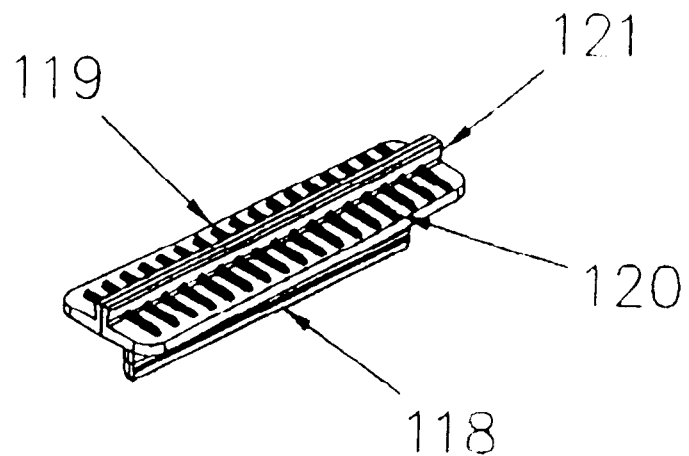
FIG. 13 shows a tray having a single projection that fits into a corresponding opening in a support.

FIG. 13 shows an aspect of a tray (119) having a projection (121) from the superior surface of said tray with anti-rotational means (120) and a single projection (118) from the inferior surface of said tray for placement in the opening of the tray support.

Figure 14:
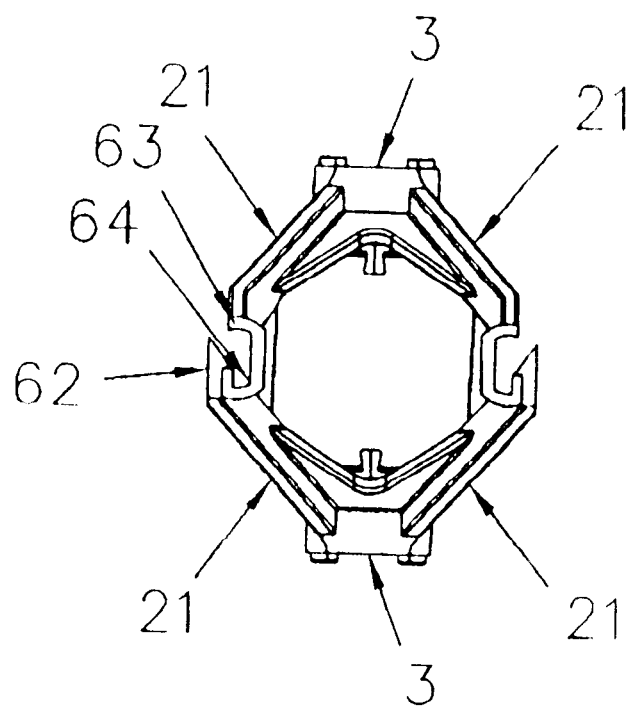
FIG. 14 shows a hinge means requiring a portion having a receptor and a prone which interacts with a curved plate.

FIG. 14 shows a hinge means requiring a receptor portion (63) and a prong (62) which interacts with a curved plate (64). The arms (21) holding the hinge portion are attached to the tray holder at the bridge (3) between the two arms.

It is understood that variations in materials, indexing means and hinge means known in the art of making devices having corresponding parts which fit into one another and/or are connected by hinge means are appropriate for use in constructing the invention.

What is claimed is:

1. A device for use in making dental models comprising a tray support a having an opening and a tray having an inferior surface with a projection from said inferior surface of said tray, wherein said projection of said tray fits into said opening in said tray support, said tray support having attached thereto hinge portions which are capable of interaction with hinge portions from a second tray support to form a completed hinge means wherein said hinge means allows for both horizontal and lateral movement.

2. The device of claim 1 wherein the hinge means is a ball joint.

3. The device of claim 1 wherein the tray projection and tray support opening are indexed in such a manner that said projection fits into said opening in only one orientation.

4. The device of claim 3 wherein the tray projection and tray support opening are indexed by means of ridges which fit into corresponding groves.

5. The device of claim 3 wherein the tray projection and the corresponding opening in the tray support are wider at one end than the other.

6. A device shaped like a horse shoe for use in making dental models comprising a tray support having an opening and a tray having a superior surface for holding casting material and an inferior surface with a projection from said inferior surface of said tray, wherein said projection of said tray fits into said opening of said tray support, said tray support having attached thereto hinge portions from a second tray support to form a completed hinge means wherein said hinge means allows for both horizontal and lateral movement.

7. The device of claim 6 wherein the hinge means is a ball joint.

8. The device of claim 6 wherein the tray projection and tray support opening are indexed in such a manner that said projection fits into said opening in only one orientation.

9. The device of claim 8 wherein the tray projection and tray support opening are indexed by means of ridges which fit into corresponding groves.

10. The device of claim 8 wherein the tray projection and tray support opening are indexed by means of waves in the sides of the projection and support openings.

11. The device of claim 6 wherein the hinge means is a prong which fits into a corresponding opening.

12. The device of claim 1 wherein the hinge means is a prong which fits into a corresponding opening.

\* \* \* \* \*